US008168294B2

(12) United States Patent
Luo et al.

(10) Patent No.: US 8,168,294 B2
(45) Date of Patent: May 1, 2012

(54) COMPOSITE

(75) Inventors: Xiaoxia Luo, HortResearch Palmerston North (NZ); Danyang Ying, HortResearch Palmerston North (NZ)

(73) Assignee: Tibone Limited, Ellerslie, Auckland (NZ)

( * ) Notice: Subject to any disclaimer, the term of this patent is extended or adjusted under 35 U.S.C. 154(b) by 782 days.

(21) Appl. No.: 11/579,523

(22) PCT Filed: May 4, 2005

(86) PCT No.: PCT/NZ2005/000090
§ 371 (c)(1),
(2), (4) Date: May 12, 2008

(87) PCT Pub. No.: WO2005/105166
PCT Pub. Date: Nov. 10, 2005

(65) Prior Publication Data
US 2008/0242529 A1  Oct. 2, 2008

(30) Foreign Application Priority Data

May 4, 2004 (NZ) ......................................... 529341
May 4, 2004 (NZ) ......................................... 529342

(51) Int. Cl.
*B32B 5/16* (2006.01)
*B22F 3/11* (2006.01)

(52) U.S. Cl. ......... 428/323; 428/325; 428/457; 428/432
(58) Field of Classification Search ................... 428/323, 428/325, 457, 432; 419/2
See application file for complete search history.

(56) References Cited

U.S. PATENT DOCUMENTS

| 4,826,156 | A | 5/1989 | Dreier |
| 5,336,465 | A | 8/1994 | Matsunaga et al. |
| 6,306,925 | B1 | 10/2001 | Clupper et al. |
| 2003/0049149 | A1 | 3/2003 | Landingham |

FOREIGN PATENT DOCUMENTS

| WO | WO 87/06842 | * 11/1987 |
| WO | WO/8706842 | 11/1987 |
| WO | WO/99/32280 | 7/1999 |

* cited by examiner

*Primary Examiner* — Gwendolyn Blackwell
(74) *Attorney, Agent, or Firm* — Greer, Burns & Crain, Ltd.

(57) ABSTRACT

A ceramic and metal composite and method of manufacture, is provided in which a ceramic phase is mixed with a metal phase to form a composite able to be applied to a substrate or formed to any shape/configuration required. For example, the composite can form, or be applied to a substrate for use as biomedical implants which can assist in and enhance osteo development or at least provide a material of better biocompatibility/bioactivity and osteo integration or infiltration with the composite. Advantageously, the ceramic and metal phases are bioactive/biocompatible. In a preferred embodiment, the composite is a homogenous mix ceramic and metal phase (and/or bioglasses) when analyzed on a micro meter scale.

49 Claims, 10 Drawing Sheets

(a) After 2 hours  (b) After 2 weeks

COMPOSITE

TECHNICAL FIELD

The present invention relates to ceramic metal composites and to processes for the production thereof. More particularly, but not exclusively, it relates to metal-ceramic composites of biocompatible metals and bioactive ceramics.

BACKGROUND ART

The clinical performance of current orthopaedic and dental implant coatings, osteobiologic (bone-filling) materials and pharmaceutical delivery systems is known to be inadequate.

The strength, integrity and osteoconduction properties of an implant/bone interface partly determine the operational life and overall performance of implants. At present, many of the materials in the art have poor osteoconduction.

The regeneration of a patient's own bone into a void is the ultimate desire of patents who require bone correction, repair or replacement. This is primary clinical goal that is not completely achievable with current technologies.

Art-skilled workers have only recently begun to develop synthetic or semi-synthetic materials for orthopaedic coatings and bone filling systems. Current technologies do not permit suitable bone integration or regeneration for either permanent integration of metal implants, or generation of new bone in void sites.

Inorganic materials constitute the mineralized frameworks that shape mammalian skeletons with the primary building block being calcium phosphate in the crystalline form hydroxycarbonate apatite (HCA) or approximated by hydroxyapatite (HA). An ageing demographic is responsible for increasing numbers of joint, tooth and bone replacement therapies being performed internationally. When bones or joints are worn, damaged, diseased or removed, the body loses the ability to repair the site. At this point artificial assistance in the form of implants must be employed. Biomaterials science has determined that a number of conditions are necessary for an implant to be successfully integrated into the skeleton. These conditions include: composition, solubility, porosity, surface chemistry and mechanical strength, but no materials simultaneously possess all of these characteristics.

The identification of soluble amorphous silicate-phosphate glasses (such as Bioglass®) in the 1980's provided a new stimulus to orthopaedic implant and osteobiologic research. The bioglass-type systems however continue to lack pore systems, are only partially resorbable and are significantly more brittle than bone. These characteristics highlight the major failings of implant coatings and bone-filling implants made from HA and Bioglass® to date. Surgeons are also increasingly being restricted in their use of autografts and allografts on comfort, cost and accessibility grounds.

In the past two years, new developments in orthopaedic and osteobiologic bone healing have occurred in the administration of growth factor proteins with implants for the augmentation of bone growth rates at surgical sites. It is likely that incorporation of growth factor proteins into coating or implant materials will stimulate rapid osteogeneration. This burgeoning new area is emerging concurrently with interesting new developments in the area of inorganic porous materials used in general pharmaceutical delivery.

At present, one of the major implant failures is caused by post-insertion loosening due to lack of interaction with the bone of the implant coating.

However, as these materials lack bioactivity, a fibril tissue layer is generated by the living body to isolate the implant materials from the natural tissue and screws, cements or locking systems are needed to secure the implant. In order to stimulate the incorporation of tissue to the implant, some bioactive materials, such as calcium phosphate, are applied to the surface of implant.

Such coatings have achieved certain success over the past several decades in stimulating early post surgical recovery and tissue incorporation, but two major problems limit their clinical use and commercial application. The first problem is the fragmentation of the coatings due to the brittle nature of the coating material and the second problem is the dissolution of the coating materials by the body fluid, leading to coating failure.

It is an object of the present invention to address the foregoing problems or at least to provide the public with a useful choice.

Further, or alternatively, an object of the present invention may be to provide a biomaterial that overcomes at least some of the above-mentioned disadvantages of the above-mentioned biomaterials and/or to provide a process for the production of the above-mentioned biomaterials, or at least to provide the public and/or industry with a useful choice.

All references, including any patents or patent applications, cited in this specification are hereby incorporated by reference. No admission is made that any reference constitutes prior art. The discussion of the reference states what their authors assert, and the applicants reserve the right to challenge the accuracy and pertiency of the cited documents. It will be clearly understood that, although a number of prior art publications are referred to herein, this reference does not constitute an admission that any of these documents forms parts of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages of the present invention will become apparent from the ensuing description which is given by way of example only.

DISCLOSURE OF INVENTION

According to a first aspect of the invention there is provided a ceramic and metal composite including or comprising:
  one or more metal or metal-rich phases, and
  one or more ceramic phases,
  wherein at least one of the metal or metal-rich phases is a biocompatible metal, and wherein at least one of the ceramic phases is a bioactive/biocompatible ceramic phase.

In a second aspect, there is provided a metal and ceramic composite comprising or including particles of a bioactive ceramic phase and/or a bioglass phase substantially homogeneously distributed within or throughout a biocompatible metal phase.

Preferably, the metal may be selected from any one or more of the following: titanium, platinum, stainless steel, gold, or mixtures thereof.

Preferably, the ceramic phase may be any bioactive ceramic.

Preferably, said bioactive ceramic may be a Calcium-Phosphate family ceramic, hydroxyapatite, powdered bone silicocalcium phosphate and/or a bioglass, said bioglass being formed from one or more of the following components: $SiO_2$, $Na_2O$, $CaO$, $P_2O_5$, $MgO$, $TiO_2$.

Preferably, the composite may include an oxidized form of one or more reducing agents, the reducing agent being able to reduce an oxidized metal phase.

Preferably, the metal phase may be titanium and the reducing agents are aluminium and/or calcium.

Preferably, the composite may be a 3-dimensional intermeshed microstructure of the ceramic and meta/metal-rich phases.

Preferably, the one or more ceramic phases may exist as particulates substantially homogenously distributed within the metal/metal-rich phase(s).

Preferably, the particulates may be in the substantially nano-metre and/or substantially micro-metre ($\mu m$) size.

Preferably, the composite may comprise particulates of $TiCaO$ with $Ca_3Al_2O_6$, dispersed substantially homogeneously within a Ti-rich phase.

Preferably, the Ti-rich phase may be $Ti_2O$.

Preferably, the composite may comprise particulates of bioactive ceramic phases dispersed substantially homogenously within a titanium metal phase.

Preferably, the composite may comprise particulates of $Al_2O_3$ and $CaO$, $Ti_2O$, $CaTiO_3$, $Al_2O_3$, $AlTi_3$, and $TiO$ dispersed substantially homogeneously within a titanium metal phase.

Preferably, the bioceramic phase and/or bioglass phase may be present in substantially spherical particles distributed substantially uniformly throughout the metal phase.

Preferably, the bioceramic phase and/or bioglass phase may be present as substantially aligned elongate particles, dispersed substantially uniformly throughout the metal phase so as to comprise a laminate structure.

Preferably, the ceramic metal composite may encourage or promote apatite growth (crystalline or otherwise) upon implantation into, or exposure to, a biological host or a biological environment (whether actual or simulated).

Preferably, the apatite growth may be a result of:
porosity of the composite, or
the presence of the particular ceramic and/or metal or metal-rich phases, or
a combination of both.

Preferably, the particles of the bioactive ceramic phase and/or bioglass phase may be of a substantially uniform size.

Preferably, the particles of the bioactive ceramic phase and/or bioglass phase may be of a size substantially within the range 1 nm-50 $\mu m$.

In a third aspect, there is provided an implant, the implant substantially made of, or substantially coated with, a composite.

Preferably, the implant may be substantially composed of a metal which is the same or different to the metal of the composite.

Preferably, the composite may be applied as a coating to said implant by any one or a combination of: plasma assisted deposition, high velocity oxy-fuel (HVOF) or high velocity low temperature spray techniques.

In a fourth aspect, there is provided a method of preparing a ceramic and metal composite comprising or including the steps of:
combining one or more reactive metal phases and an oxidized biocompatible metal phase to form a mixture;
milling the mixture;
heating the mixture sufficiently to enable a solid state reaction to take place,
wherein the resulting ceramic and metal composite includes or comprises:
one or more metal or metal-rich phases, and
one or more ceramic phases,
wherein at least one of the metal or metal-rich phases is or includes the bioactive metal, and wherein at least one of the ceramic phases is a bioceramic phase.

In a fifth aspect, there is provided a method of preparing a ceramic and metal composite, comprising or including the steps of:
combining a biocompatible metal and a bioactive ceramic and/or bioglass phase to form a mixture; and
high energy milling the mixture in the absence of oxygen until a composite is formed, wherein the composite comprises a substantially homogenous distribution of the bioactive ceramic phase within the biocompatible metal phase.

Preferably, the step of milling the mixture continues until the mixture may be substantially homogenous at the micrometer scale.

Preferably, the step of milling of the mixture continues until the mixture may be substantially homogenous at the nanometre scale.

Preferably, the particles of the bioactive ceramic phase and/or bioglass phase may be of a substantially uniform size.

Preferably, the particles of the bioactive ceramic phase and/or bioglass phase may be substantially in the size range of 1 nm to 50 $\mu m$.

Preferably, the particles of the bioactive ceramic phase and/or bioglass phase may be substantially in the size range of 1 nm to 100 nm.

Preferably, the oxidized biocompatible metal phase may be a metal oxide phase.

Preferably, the method of the invention may be carried out in the absence of oxygen.

Preferably, the method may include removing oxygen from the mixture milling environment prior to milling.

Preferably, the absence of oxygen may be achieved by substitution oxygen with a noble gas.

Preferably, the as milled powder may be used as feedstock for high velocity low temperature spray coating directly.

Preferably, the as milled powder may be compressed into a near-net shape of an orthopaedic part and sintered using conventional powder metallurgy method.

Preferably, the as milled powder may be formed to an orthopaedic component using fast prototyping techniques.

Preferably, heating of the mixture may take place at a temperature to enable the solid state reaction to take place.

Preferably, heating of the mixture may take place at a temperature exceeding substantially 500° C.

Preferably, heating of the mixture may take place at or a temperature exceeding substantially 1000° C.

Preferably, the heating step may take substantially one hour.

Preferably, the heating step may take less than substantially one hour.

Preferably, the heating step may take longer than substantially one hour.

Preferably, the method may include the step of sintering the milled composite.

Preferably, the milling step can be varied in order to produce a composite of particular characteristics.

Preferably, it may be the duration of the milling step that is altered.

Preferably, the step of milling the mixture may be selected to produce a composite wherein the bioceramic phase and/or bioglass phase is present in substantially spherical particles distributed substantially uniformly throughout the metal phase.

Preferably, the step of milling the mixture may be selected to produce a composite wherein the bioceramic phase and/or bioglass phase is present as substantially aligned elongate particles, dispersed substantially uniformly throughout the metal phase so as to comprise a laminate structure.

Preferably, in order to substantially assist osteointegration of the composite, the composite may be substantially porous.

Preferably, in order to substantially assist osteointegration of the composite, the composite may be substantially dense and becomes porous substantially porous in situ over time.

Advantageously, the composite described above provides a suitable substrate to which organics, such as bone, can attach itself thereto, as well as preferably integrate with. Desirably, a substantially homogenous composite of ceramic and metal phases allows enhanced osteointegration. A more homogenous composite also allows for greater consistency of implant or bone interface characteristics such as porosity, strength, integrity and osteo conduction properties. The encouragement of at least allowability for regeneration of a patient's own bone into a void, and/or connectivity or attachment of an organism or organic material to the composite (whatever shape or form it may be in) is preferred.

Definitions:

Biocompatible metal Metals which are compatible with the biological environment. Such metals include Ti, Ti-6Al-4V, stainless steel, gold and silver, etc.

Bioactive ceramic A ceramic having an effect (ideally favourable) on a biological species. Bioactive ceramics include the Ca—P family, and bioactive glasses, such as $SiO_2$, $Na_2O$, $CaO$, $P_2O_5$, $MgO$, $TiO_2$ in specific proportions.

Reactive Metal A metal that not only readily combines with oxygen at elevated temperatures to form very stable oxides but is also more reactive than the other metal concerned (e.g. titanium, gold, stainless steel, or other biocompatible metal) and able to take oxygen from the oxides of these metals.

In the present invention biocompatible and bioactive are generally interchangeable, both of which should not be materials which may be rejected by an organism, such as a human or animal patient(s).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

Other aspects of the invention may become apparent from the following description which is given by way of example only and with reference to the accompanying drawing(s).

BEST MODES FOR CARRYING OUT THE INVENTION

Figure 1:
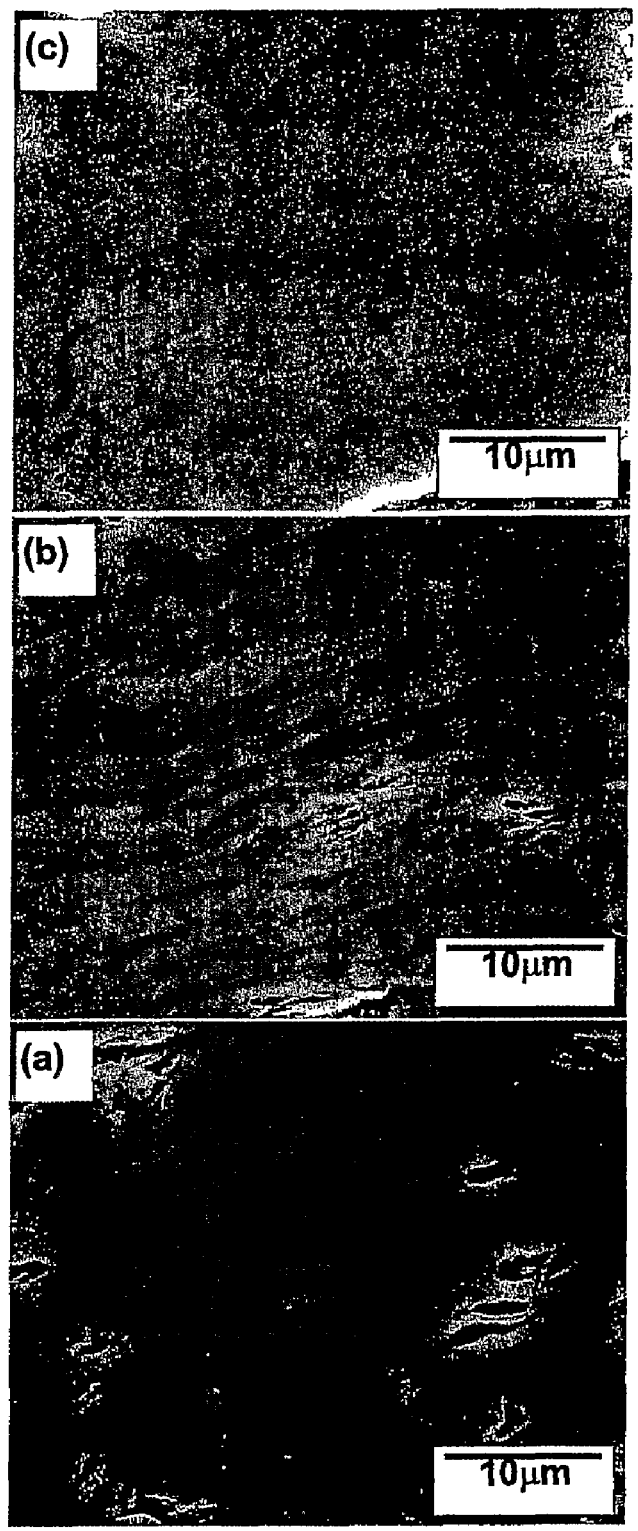
FIG. 1 shows SEM (Scanning Electron Microscope) micrograph of a composite Ti/Ca—P powder produced after milling for (a) 1 hr, (b) 2 hrs and (c) 4 hrs

As stated, in the present invention provides a multilayered composite or metal matrix composite comprising a metal phase and a bioceramic and/or bioglass phase.

The idea of a Ti/bioceramics composite is to combine the advantages of the mechanical properties and bone bonding capabilities of bioceramics. Such biocomposite is highly desirable for load bearing bone repairing applications. However, industry is unable to take full advantage of such concept if the metal phase and bioceramic phase are coarsely interconnected. Many researchers reported successful development of Ti/bioceramic composite in the past either using convention powder metallurgy techniques 5-9 or using plasma spray techniques 10-12. These techniques all produce composites with metal and bioceramic phases interconnected at micrometer scales. Present research conducted by authors has lead to the development of a class of Ti/bioceramics composites with a metal and bioceramic phases interconnected at sub-micrometer to nanometer scales.

As stated, the present invention provides a 3-D intermeshed composite comprising one or more metal phases and one or more ceramic phases. This structure indicates two or more different materials present in different phases within the one composite. Each phase is present in nm-μm dimensions and is interconnected with the others by chemical bonds.

Preferably, the metal phase is a biocompatible metal, such as (but not limited to) titanium, platinum, gold or stainless steel or mixtures thereof. Titanium is currently particularly preferred.

The ceramic phase is any bioactive ceramic, such as Ca—P family, or bioglass, such as $SiO_2$, $Na_2O$, $CaO$, $P_2O_5$, $MgO$, $TiO_2$ in specific proportions. Currently preferred examples include calcium phosphate, hydroxyapatite, powdered bone silico-calcium phosphate and Bioglass.

When an implant is coated in a composite of the invention, the composite may, for example, be applied as coatings to implants by plasma assisted deposition, high velocity oxy-fuel (HVOF) or high velocity low temperature spray techniques.[1,2]

Suitable substrate metals for an implant to be coated include but are not limited to titanium and stainless steel. The metal phase and the substrate metal may be the same or different.

As stated above, the present invention is also directed to a process for the production of a composite comprising the steps of (in the absence of oxygen):

1. combining a metal phase metal and one or more bioceramic phases to form a mixture;

2. high energy milling the mixture in the absence of oxygen until a composite is formed.

The invention also includes the method of preparation of the novel composite material, which in the preferred embodiment comprises the steps of (in the absence of oxygen from the environment):
1. combining one or more reactive metal phases (ideally aluminium and/or calcium) and a $TiO_2$ phase to form a mixture;
2. milling the mixture until the mixture becomes homogenous at the micrometer scale;
3. heating the mixture sufficiently to enable a solid state reaction to take place.

The absence of oxygen may be achieved using any known method in the art. Substitution with a noble gas is the currently preferred method of the inventors.

The process may also include the further step of sintering the milled composite.

Generally, heating of the mixture takes place at a temperature exceeding 500° C., preferably at a temperature at or exceeding 1000° C. to enable the solid state reaction to take place. The exact conditions must be tailored to the agents used and the type of composite desired.

Preferably, the heating step takes about one hour.

In order to maximize the osteointegration of a composite of the present invention, the composite should be made porous. Alternatively, the composite may be made substantially dense providing it becomes porous in situ over time.

The composite of the invention is a cermet. Cermets are composite materials in which ceramic and metal particles are strongly bound together. Such materials can simultaneously exhibit the properties of both the ceramic and the metal components of the composite. This allows cermet properties to be highly tailored to favour high wear resistance, high malleability or points in between.

The preparation of Ti/hydroxyapatite (HA), Ti/powdered bone and Ti/silico-calcium phosphate or bioglass cermets will provide materials with tailored compositional and microstructure properties for the formation of bioactive coatings on orthopaedic implant surfaces. Preferably, the composites of the present invention provide a 3-dimensional microstructure for strong interlocking of the bone at the growth front. The bioactivity of the cermet will be affected by a number of factors such as chemical composition, metal/ceramic mass and volume fraction, particle morphology and porosity. An art-skilled worker is able to manipulate these features to produce optimal cermet materials via the methods herein. Coatings are be prepared using well-established techniques.

PREPARATION

Using the teachings herein, cermet materials of the invention can be developed using the following synthesis route of high energy mechanical milling.

The inventors have found that, for example, Ti-bioceramic cermets can be produced by high-energy mechanical milling of a mixture of Ti powder and bioceramic powder. The composition and porosity of the cermet can be controlled to suit the requirements for osteoconduction.

By appropriately adjusting the conditions for the formation of the cermet, the formation of bioactive cermets through the powders formed from HA, microparticulate processed bone or Bioglass is possible.

A multilayered composite microstructure may be formed in accordance with the present invention. The microstructure can be modified and controlled through manipulation of the milling conditions, such as but not limited to the milling time. Some adverse reactions may occur in the process. A good understanding of the processing conditions required for a particular application is the key to gaining full control of the phase formation and the microstructure of the composite material. Art-skilled workers, given the teachings herein, would be able to formulate such conditions to enable the formation of a required composite for their needs with minimal experimentation.

A 3-D intermeshed composite microstructure may be formed in accordance with the present invention. The microstructure can be modified and controlled through manipulation of the milling conditions, such as but not limited to the milling time and charge ratio. The charge ratio is defined as the ratio of the weight of the milling media, such as balls or disks, and the weight of the materials to be milled. Some adverse reactions may occur in the process. A good understanding of the processing conditions required for a particular application is the key to gaining full control of the phase formation and the microstructure of the composite material. Art-skilled workers, given the teachings herein, would be able to formulate such conditions to enable the formation of a required composite for their needs with minimal experimentation.

Using the teachings herein, cermet materials of the invention can be developed using the following synthetic route:

The inventors have shown that, for example, $TiO_2$ has the potential to be partially reduced to Ti metal by more active metals such as Al or Ca. This allows the formation of intermeshed 3-D metal/ceramic composites. Reaction conditions can be varied using techniques in the art to manipulate the kinetics of the reactions to control of the microstructure of the cermet composites formed.

Intermeshed 3-dimensional composite structures are preferred to laminate type arrangements as they tend to have or provide greater strength and other structural characteristics in multiple dimensions. This is especially preferred when the composite is used as the material for an implant itself, and/or so that its integrity is not easily damaged by impacts.

The use of a homogenous material (composite) also allows greater infiltration of bone or organic organism with the composite or implant, and therefore better integration with each other. Accordingly, the finer the size of the pores on the composite (once porous) the (generally) higher the number of pores into which integration and infiltration, and therefore enhanced and greater number of contacts or contact points/pores. An in-homogenous composite, whilst it may also have a porous structure if designed as such, would not provide a regular arrangement of pores upon which contact points and infiltration or integration could occur with. It is preferably that the regular and consistent pores provide enhanced integration. Accordingly, whilst a material, when viewed at a macro-scale, can appear homogenous, at a micro-scale, for example on a micro-scale (or even better when on a nano particle sized scale) can appear in-homogenous.

The applicants have realised that smaller particles, whilst harder to achieve, and mix to a homogenous state, provide a preferred composite. For example 1 nano-metre sized particles can achieve a very fine/small sized pore, but in a homogenous state, can provide a higher number of pores and more consistently arranged/distributed throughout the composite for integration with a material which infiltrates the pores.

In a currently preferred solid-state process, the initial powder mixture is mechanically milled to form a homogeneous mixture of $TiO_2$ and reactive metal(s) at the micrometer scale. This mixture is then heated in a controlled manner to initiate the solid-state reaction, which transforms the $TiO_2$ and active metal into Ti metal or Ti alloy and new oxides, such as $Al_2O_3$ or CaO, depending on the active metals used. In the research proposed here, this technique will be modified to permit the formation of bioactive ceramic-Ti cermets by changing the ceramic component to form bioactive calcium phosphates and silico-calcium phosphates during the solid-state reaction process.

Application of the Composite of the Invention

Composites of the present invention find application in coatings and in bone repair and development.

The composites may be pressed into pellets and sintered at low temperatures so to avoid changes to microstructure and crystallinity. These pellets are readily testable for bioactivity.

The currently preferred method for application of the composites of the invention to a substrate metal is plasma-spraying. In this technique, composite particles are injected into a plasma flame where the particles are rapidly heated and accelerated to high velocity. The hot material impacts on the substrate surface and rapidly cools forming a coating. Many operational parameters affect the coating, such as the distance of the substrate from the plasma, current, anode-cathode gap distance, gas mixture, the position at which the powder enters the plasma stream, and the spray environment (atmosphere or vacuum). These parameters may be varied to suit the particular application.

An alternative coating method is High Velocity Oxy-Fuel (HVOF). In this technique, a carrier gas is employed that is not ionized and the temperatures generated are considerably lower than in plasma spraying. This technique is particularly useful to flow into irregularities in the surface of the substrate because of the much higher velocity of the composite particles causes them to readily fuse or sinter. This technique tends to enable the crystallinity and microstructure of the coating materials to be maintained.

Another alternative coating method is Low Temperature High Velocity Spray. In this technique, a carrier gas is employed that is not ionized and the temperatures generated are considerably lower than in plasma spraying and HVOF. This technique is particularly useful to flow into irregularities in the surface of the substrate because of the much higher velocity of the composite particles causes them to readily fuse or sinter. This technique tends to enable the crystallinity and microstructure of the coating materials to be maintained.

The invention will now be described below with reference to non-limiting examples:

EXAMPLE 1

Formation of a Ti/Ca—P Composite

Titanium (Aldrich, 99.98% pure, −325 mesh) and β-tricalcium phosphate ($Ca_3(PO_4)_2$) (Fluka, >=96.0% pure) powders were used as starting materials. A powder mixture of 10 grams Ti and $Ca_3(PO_4)_2$ powder with a volume ratio of 1:1 was placed in a hardened stainless steel vial. The system was evacuated and re-filled with argon several times (argon 'protection'), and the vial was then sealed under argon protection. A Spex 9000 Mixer/Mill was used for the milling. Powder extracts were taken after mixing for 1, 2 and 4 hours.

EXAMPLE 2

Characterisation of Composite

The milled powder extracts from Example 1 were subjected to microstructure characterisation using a Hitachi 54000 scanning electron microscope (SEM), which was equipped with a Kevex microanalyser for energy dispersive x-ray analysis (EDX). The milled powders were also examined using an X-ray differactometry (XRD).

Figure 2:
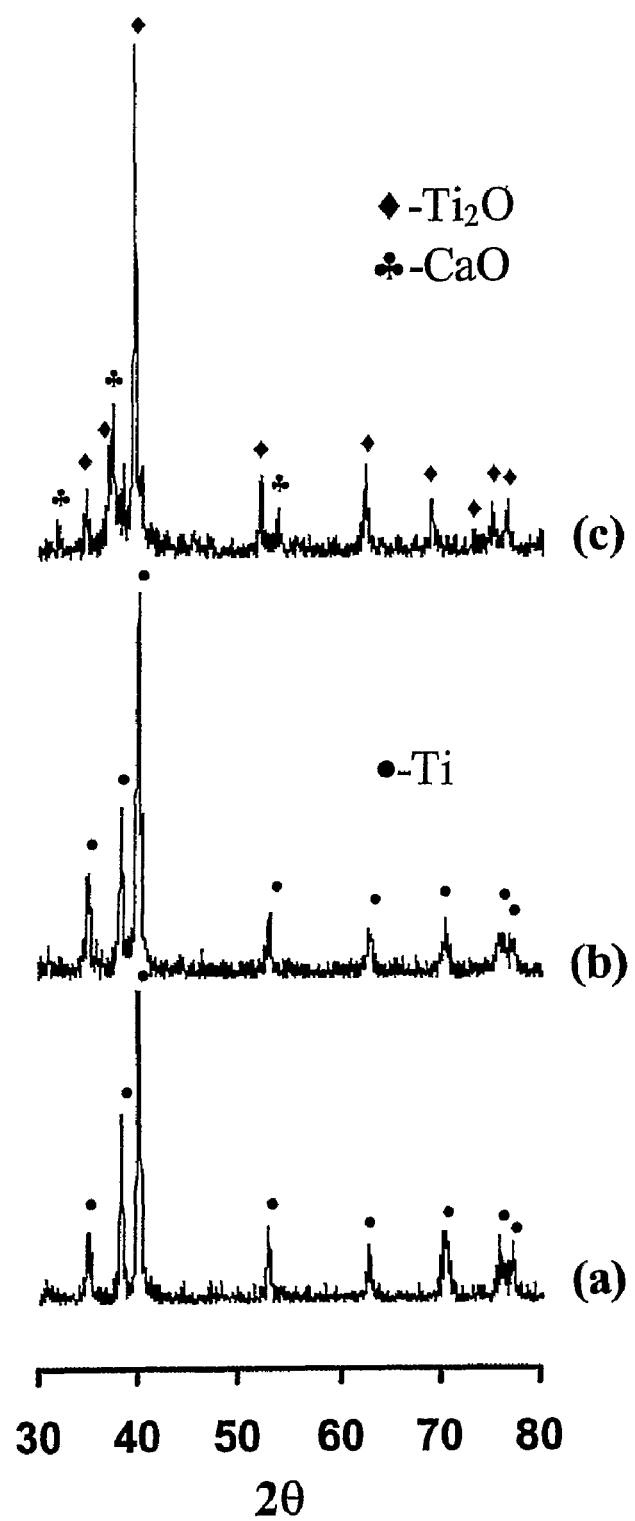
FIG. 2 shows XRD (X-Ray diffractometry) patterns of the composite powders shown in FIG. 1.

Titanium/calcium phosphate composite powder was produced after the above powder mixture was milled for 1 hour. Each individual powder particle exhibited a multilayered microstructure, as shown in FIG. 1(*a*). EDX analysis indicated that the light phase is Ti and the dark phase is Ca and P rich. The thickness of Ti layer ranged from 1 to 5 μm, and averaged about 3 μm. There are some dark areas that became porous. XRD scan of the 1 hour milled powder showed strong Ti peaks. No $Ca_3(PO_4)_2$ peaks were detected, as shown in FIG. 2(*a*).

The multilayered composite microstructure was refined when the milling time increased from 1 hour to 2 hours, as shown in FIG. 1(*b*). The average Ti layer thickness was estimated to be about to 2 μm. XRD scan of this powder still showed strong Ti peaks and no other significant peaks were detected, as shown in FIG. 2(*b*).

Solid state reactions occurred when the powder was milled for 4 hours. This is evident from the XRD scan of the 4 hours milled powder, as shown in FIG. 2(*c*). The major phase in this powder is Ti ($Ti_2O$) and a new minor phase is CaO. SEM characterisation as shown in FIG. 1(*c*) showed that the multilayered microstructure still remained in the powder particle but with a much smaller layer thickness of about a few hundred nanometers.

Figure 9:
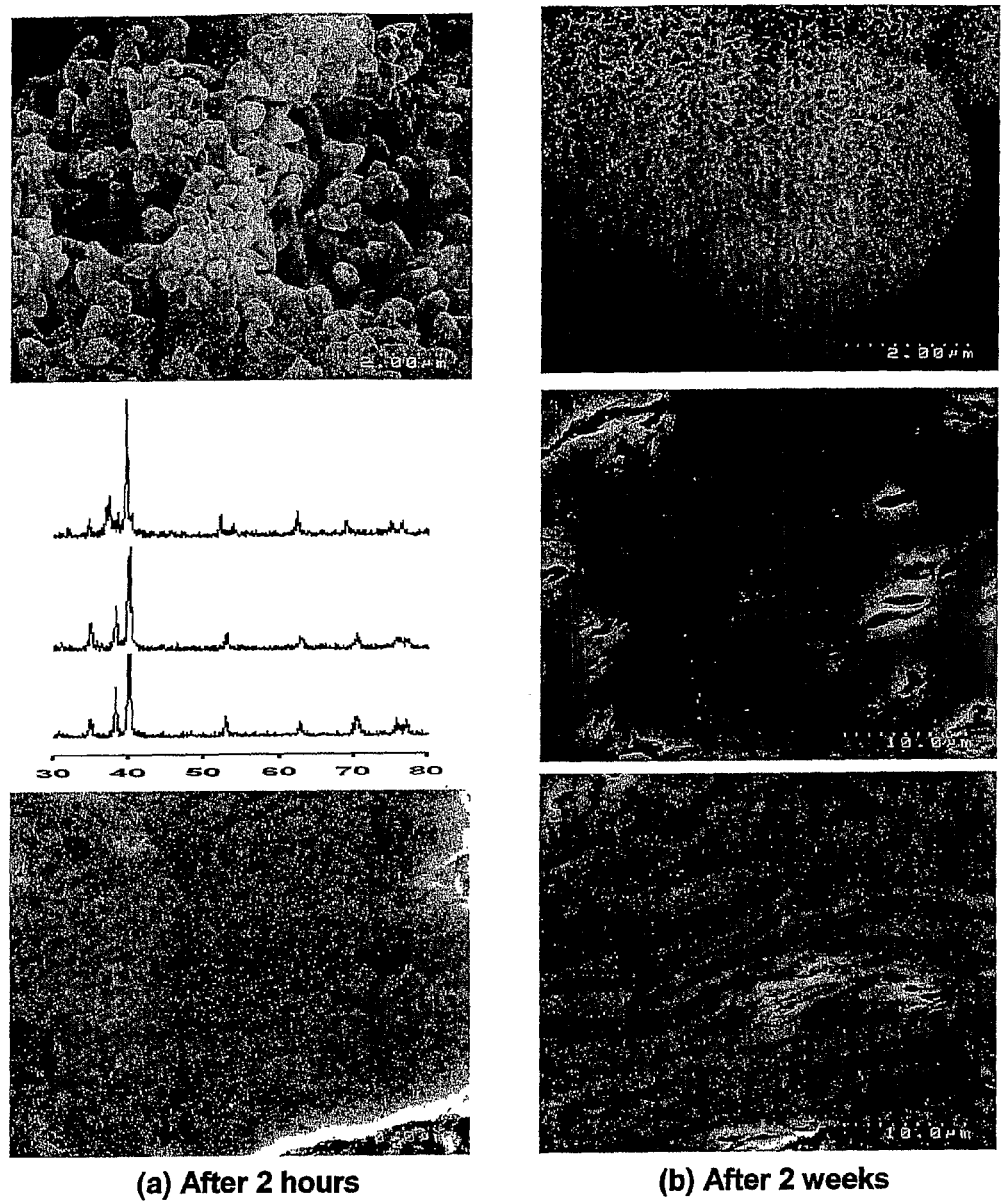
FIG. 9 illustrates SEM surface morphology of the composite after SBF immersion.

FIG. 9 shows some SEM morphologies of the composite surface after the composite was immersed in SBF for two hours and two weeks respectively. Ca—P apatite was easily deposited on the surface of the composite.

Figure 10:
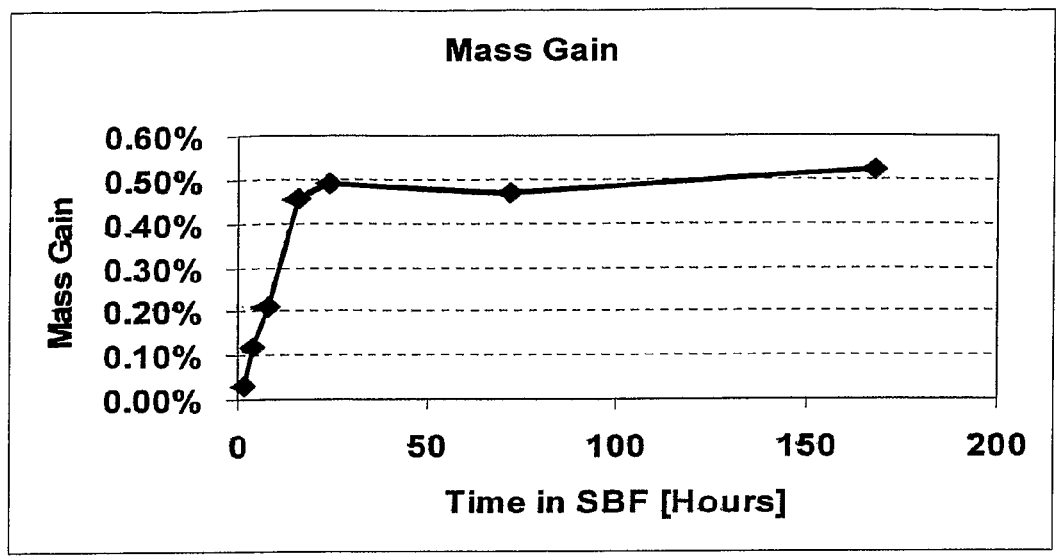
FIG. 10 illustrates how the mass gain of the composite over time when immersed in SBF.

FIG. 10 shows the mass gain of the composite when it was immersed in SBF. The mass increased very quickly during the first 14 hours and then slowed down. The incubation time for the apatite to nucleate and grow is very short. This indicates that the composite is highly bioactive.

In these examples, the Ti/calcium-phosphate composite powder was fabricated using high energy milling. The Ti—CaP intermeshed microstructure can be controlled and refined to sub-micrometer to nanometer scales. And, the composite is highly bioactive and can be used as a suitable biomedical material for load bearing bone repairing applications.

EXAMPLE 3

Titanium Alloy/Alumina/Calcium-Phosphatecomposite

A total of 10 g powder mixture of $TiO_2$ (APS Chemicals, 99% pure), Al (APS Chemicals, 40 μm particle size, >99% pure) and Ca (APS Chemicals, granules), stoichiometrically according to the reaction equation (1), was placed in a hardened steel vial with four ½-inch stainless steel balls. The system was evacuated and re-filled with argon several times, and the vial was then sealed under argon protection. A Spex 9000 Mixer/Mill was used for the milling. The powder mixture was milled for 4 hours. The milled powder was pressed into a pellet of 15 mm diameter and 3 mm thickness. The pellet was then sintered in a vacuum furnace at 1000° C. for 1 hour (an inert environment).

$$6TiO_2 + 4Al + 6Ca = 6Ti + 2Al_2O_3 + 6CaO \tag{1}$$

EXAMPLE 4

Testing of Sintered Pellet

The sintered pellet of Example 3 was subjected to characterization using a scanning electron microscope (SEM), which was equipped with an energy dispersive x-ray analyzer (EDX), and X-ray differactometry (XRD). The pellet was also tested for in vitro bioactivity using a simulated body fluid (SBF) prepared in accordance with T. Kokubo, H. Kushitani, S. Sakka, T. Kitsugi and T. Yamamuro, "Solutions able to reproduce in vivo surface-structure changes in bioactive glass-ceramic A-W", *J. Biomed. Mater. Res.*, 24, 721-734 (1990), which is hereby incorporated in its entirety by reference. After 7 days of immersion in the SBF, the pellet was examined for mineral deposition using SEM.

Figure 3:
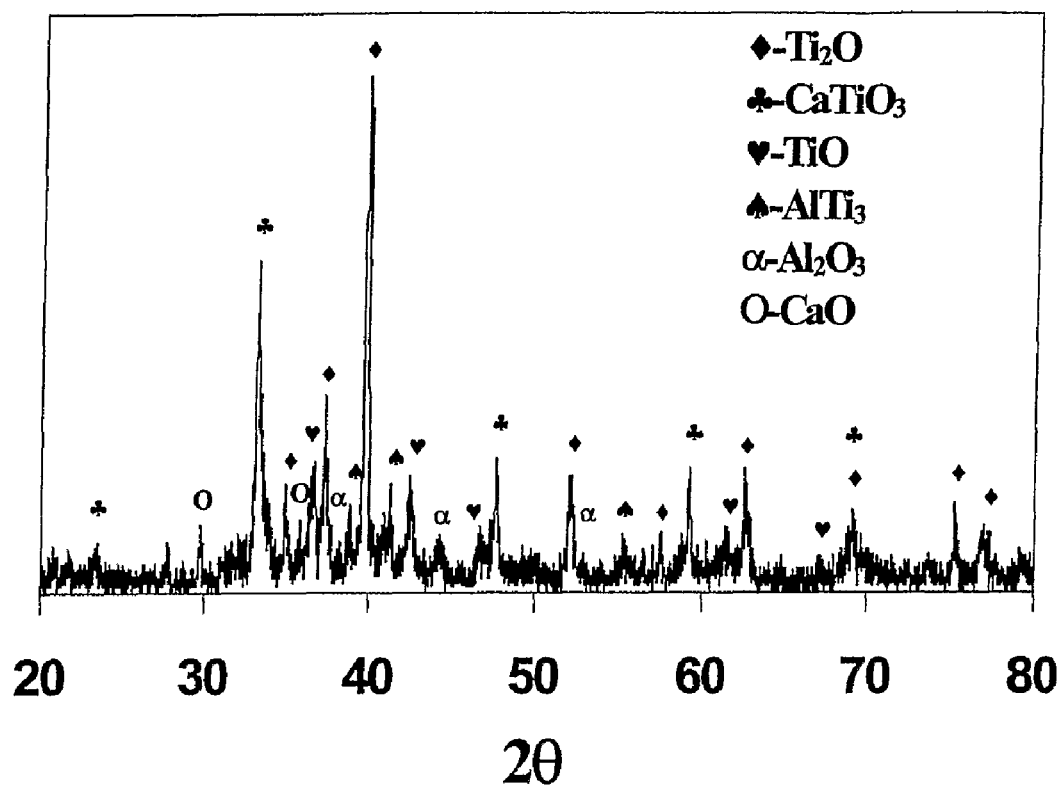
FIG. 3 shows XRD Patterns of a Ti alloy/$Al_2O_3$/$CaTiO_3$ composite material.
Figure 4:
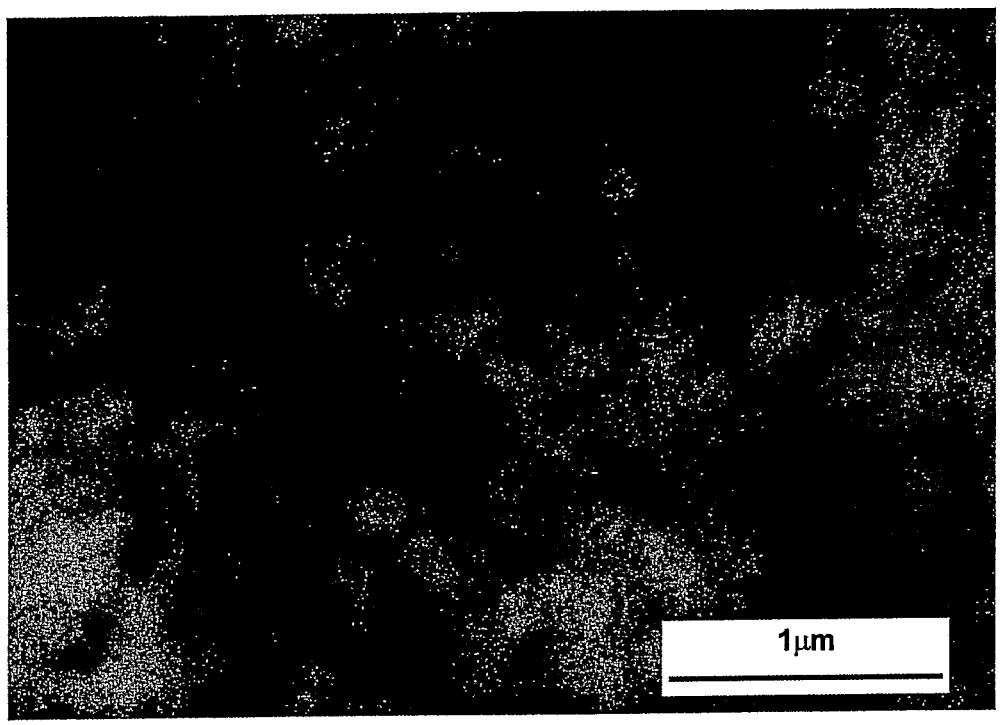
FIG. 4 shows a SEM micrograph of the composite material of FIG. 3.
Figure 5:
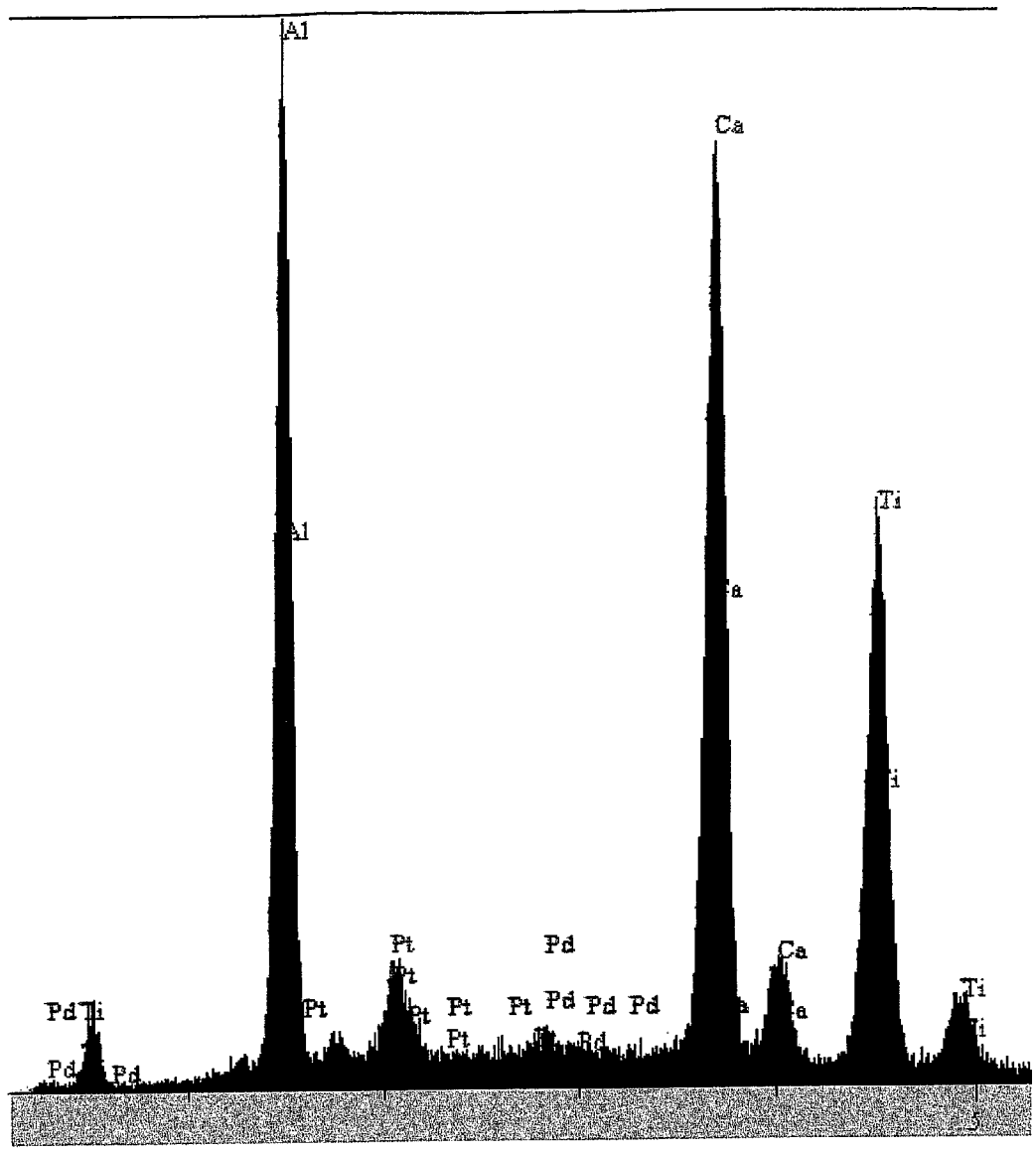
FIG. 5 shows an EDX (Energy Dispersive X-ray analysis) Spectrum of the Dark Phase of the composite material of FIG. 4.
Figure 6:
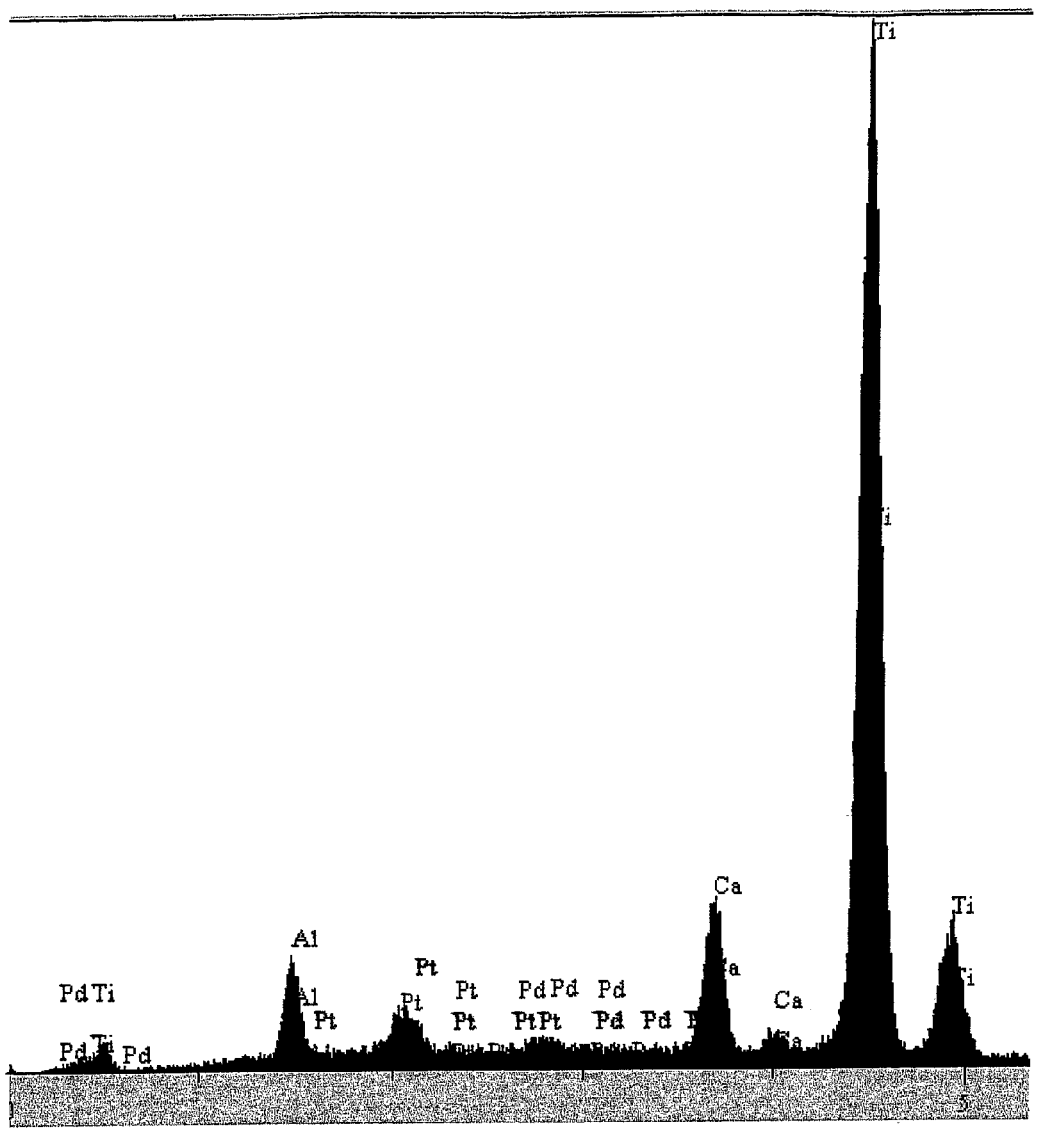
FIG. 6 shows an EDX Spectrum of the Light Phase of the composite material of FIG. 4.
Figure 7:
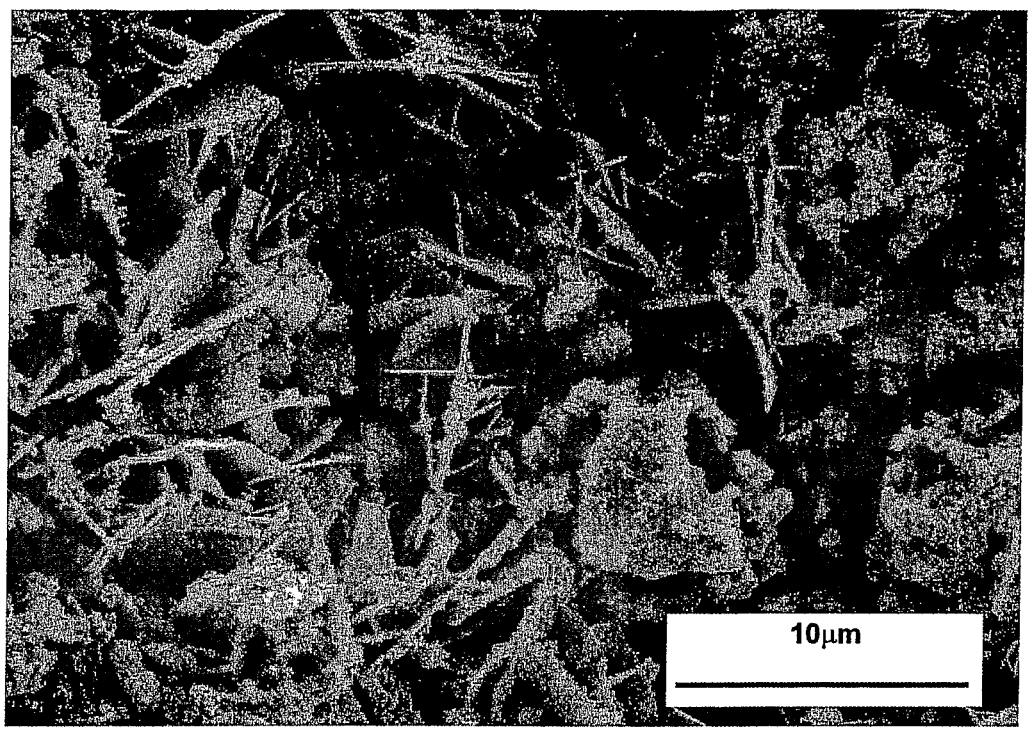
FIG. 7 shows a SEM image of the surface of the composite material of FIG. 4 after immersed in Simulated Body Fluid (SBF) for 7 days.

A composite with major phases of $Ti_2O$ and $CaTiO_3$ and minor phases of TiO and $AlTi_3$ was produced using a combination of high energy ball milling and heat treatment as shown in the XRD of FIG. 3. SEM examination of this composite material showed a closely intermeshed microstructure at sub-micrometer to nanometer scale, as shown in FIG. 6. EDAX analysis showed that the light phases were Ti rich phases (FIG. 5) and the dark phases were Al/Ca rich phases (FIG. 6). An in-vitro bioactivity test using SBF showed that Ca—P apatite could easily nucleate and grow from the surface of this composite, as shown in FIG. 7.

EXAMPLE 5

Further Testing of Pellet

Pellets from Example 1 were cut into specimens of two sizes of $10 \times 5 \times 2$ mm$^3$ and $6 \times 4 \times 2$ mm$^3$ and ground using 500 grid SiC sandpaper. Each of the specimens was washed ultrasonically in acetone, absolute alcohol and deionized water for 10 minutes. The specimens were then dried in an incubator. A control specimen of Ti-6Al-4V alloy was cut to similar size and prepared using the same procedure.

Three sets of specimens were immersed in three containers of SBF. The SBF was prepared in accordance with the protocol by Kokubo et al (Supra). In summary, the protocol involved dissolving reagent chemical of NaCl, $NaHCO_3$, KCl, $K_2HPO_2H_2O$, $MgCl_2.H_2O$, CaCl and $Na_2SO_4$ in deionized water. The pH values of the SBF in three containers were measured every 24 hours for 7 days.

Figure 8:
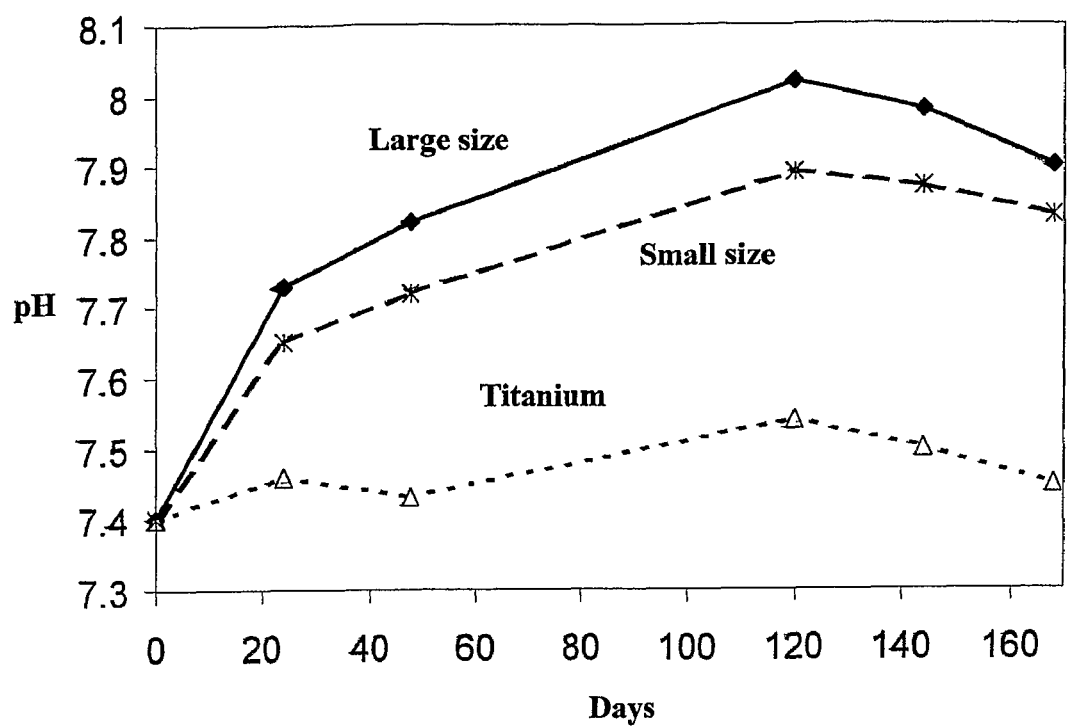
FIG. 8 illustrates changes in the pH value of the SBF as a function of immersion time using a composite of FIG. 7.

The results of the test are as depicted in FIG. 8. The pH values of both composite samples increased significantly compared with the control specimen. This indicates that a reaction between the CaO in the specimen and SBF occurred. The pH value of the SBF containing the bigger composite sample showed a larger pH value increase due to the larger sample having a larger surface area for reaction with the SBF. SEM surface morphology examination of the specimen showed obvious nuclei and apatite deposition. EDX analysis showed that the crystallite apatite was Ca and P rich, indicating the present of Calcium phosphate (apatite).

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

In addition, where features or aspects of the invention are described in terms of Markush groups, those skilled in the art will recognise that the invention is also thereby described in terms of any individual member or subgroup of members of the Markush group.

Aspects of the present invention have been described by way of example only and it should be appreciated that modifications and additions may be made thereto without departing from the scope thereof as defined in the appended claims.

[1] Larry L. Bench & June Wilson, An Introduction to Bioceramics, World Scientific, 1993.
[2] W. R, Lacefield, "Hydroxyapatite Coatings," in Bioceramics; Material Characterisation Versus In Vivo Behaviour, eds. P. Ducheyne and J. E. Lemons. (Ann. NY. Acad. Sci, 1988), VoL 523, pp. 72-80.
[3] Larry L. Bench & June Wilson, An Introduction to Bioceramics, World Scientific, 1993.
[4] W. R, Lacefield, "Hydroxyapatite Coatings," in Bioceramics; Material Characterisation Versus In Vivo Behaviour, eds. P. Ducheyne and J R Lemons. (Ann. NY. Acad. Sci., 1988), Vol. 523, pp. 72-80.
[5] C. Q. Ning and Y. Zhou, Biomaterials 23 (2002) 2909.
[6] G Z Zhang, G L Zhang, T X Zhong, J X Zhang, D T Zhang, Patent CN 1382660A (2002).
[7] C L Chu, J C Zhu, Z D Yin and P H Lin, Materials Science and Engineering A348 (2003) 244.
[8] E Verne, M Ferraris, C Jana and L Paracchini, J. of European Ceramic Society 20 (2000) 473.
[9] E Verne, E Bona, E Angelini, F Rosalbino, P Appendino, J. of European Ceramic Society 22 (2002) 2315
[10] Y. W. Gu, K. A. Khor and Cheang, Biomaterials 24 (2003) 1603.
[11] K. A. Khor, Y. W. Gu, C. H. Quek and P. Cheang, Surface and Coatings Technology 168 (2003) 195.
[12] K. A. Khor, Y. W. Gu, C. H. Quek and P. Cheang, Surface and Coatings Technology 168 (2003) 195.

The claims defining the invention are:

1. A ceramic and metal composite comprising:
   one or more metal or metal-rich phases,
   one or more ceramic phases, and
   an oxidized form of one or more reducing agents, the reducing agent being able to reduce an oxidized metal phase,
   said one or more metal or metal-rich phases and said one or more ceramic phases being different phases,
   wherein at least one of the metal or metal-rich phases is a biocompatible metal, and wherein at least one of the ceramic phases is a bioactive ceramic phase.

2. A metal and ceramic composite comprising particles of at least one of a bioactive ceramic phase and a bioglass phase substantially homogeneously distributed within or throughout a biocompatible metal phase, and an oxidized form of one or more reducing agents, wherein said bioactive ceramic phase and said bioglass phase are different phases.

3. The composite as claimed in claim 1, wherein the metal is selected from at least one of the group consisting of: titanium, platinum, stainless steel, gold and mixtures thereof.

4. The composite as claimed in claim 1, wherein the ceramic phase is any bioactive ceramic.

5. The composite as claimed in claim 1, wherein said bioactive ceramic is at least one of a Calcium-Phosphate family ceramic, hydroxyapatite, powdered bone silico-calcium phosphate and a bioglass, said bioglass being formed from at least one of the components selected from the group consisting of: $SiO_2$, $Na_2O$, CaO, $P_2O_5$, MgO, $TiO_2$.

6. The composite as claimed in claim 1, further comprising a reducing agent, wherein the metal phase is titanium and the reducing agent is at least one of aluminum and calcium.

7. The composite as claimed in claim 1, wherein the composite is a 3-dimensional intermeshed microstructure of the ceramic and metal/metal-rich phases.

8. The composite as claimed in claim 1, wherein the one or more ceramic phases exist as particulates substantially homogenously distributed within the metal/metal-rich phase (s).

9. The composite as claimed in claim 8, wherein a size of the particulates is between a nano-meter and a micro-meter (μm).

10. The composite as claimed in claim 1, wherein the composite comprises particulates of TiCaO with $Ca_3Al_2O_6$, dispersed substantially homogeneously within a Ti-rich phase.

11. The composite as claimed in claim 10, wherein the Ti-rich phase is $Ti_2O$.

12. The composite as claimed in claim 1, wherein the composite comprises particulates of bioactive ceramic phases dispersed substantially homogeneously within a titanium metal phase.

13. The composite as claimed in claim 1, wherein the composite comprises at least one of the particulates selected from the group consisting of: $Al_2O_3$ and CaO $Ti_2O$, $CaTiO_3$, $Al_2O_3$, $AlTi_3$, and TiO dispersed substantially homogenously within a titanium metal phase.

14. The composite as claimed in claim 1, wherein the bioceramic phase and/or bioglass phase is present in substantially spherical particles distributed substantially uniformly throughout the metal phase.

15. The composite as claimed claim 1, wherein the bioceramic phase and/or bioglass phase is present as substantially aligned elongate particles, dispersed substantially uniformly throughout the metal phase so as to comprise a laminate structure.

16. The composite as claimed in claim 1, wherein the composite encourages or promotes apatite growth (crystalline or otherwise) upon implantation into, or exposure to, a biological host or a biological environment (whether actual or simulated).

17. The composite as claimed in claim 1, wherein the apatite growth is a result of:
porosity of the composite, or
the presence of the particular ceramic and/or metal or metal-rich phases, or
a combination of both.

18. The composite as claimed in claim 1, wherein the particles of the bioactive ceramic phase and/or bioglass phase are of a substantially uniform size.

19. The composite as claimed in claim 1, wherein the particles of the bioactive ceramic phase and/or bioglass phase are of a size substantially within the range 1 nm-50 μm.

20. An implant, substantially made of, or substantially coated with, a metal composite as claimed in claim 1.

21. The implant as claimed in claim 20, wherein when the implant is a substrate, said substrate is substantially composed of a metal which is the same or different to the metal of the composite as claimed claim 1.

22. The implant as claimed in claim 20, wherein the composite is applied as a coating to said implant by any one or a combination of: plasma assisted deposition, high velocity oxy-fuel (HVOF) or low temperature high velocity spray techniques.

23. A method of preparing a ceramic and metal composite as claimed in claim 1, comprising or including the steps of:
combining one or more reactive metal phases and an oxidized biocompatible metal phase to form a mixture;
milling the mixture;
heating the mixture sufficiently to enable a solid state reaction to take place, wherein the resulting ceramic and metal composite includes or comprises:
one or more metal or metal-rich phases, and
one or more ceramic phases,
wherein at least one of the metal or metal-rich phases is or includes the bioactive metal, and wherein at least one of the ceramic phases is a bioceramic phase.

24. A method of preparing a ceramic and metal composite as claimed in claim 1, comprising or including the steps of:
combining a biocompatible metal and a bioactive ceramic and/or bioglass phase to form a mixture; and
high energy milling the mixture in the absence of oxygen until a composite is formed, wherein the composite comprises a substantially homogenous distribution of the bioactive ceramic phase within the biocompatible metal phase.

25. The method as claimed in claim 23, wherein the step of milling the mixture continues until the mixture is substantially homogenous at the micrometer scale.

26. The method as claimed in claim 23, wherein the step of milling the mixture continues until the mixture is substantially homogenous at the nanometer scale.

27. The method as claimed in claim 23, wherein the particles of the bioactive ceramic phase and/or bioglass phase are of a substantially uniform size.

28. The method as claimed in claim 23, wherein the particles of the bioactive ceramic phase and/or bioglass phase are substantially in the size range of 1 nm-50 μm.

29. The method as claimed in claim 23, wherein the particles of the bioactive ceramic phase and/or bioglass phase are substantially in the size range of 1 nm to 100 nm.

30. The method as claimed in claim 23, wherein the oxidized biocompatible metal phase is a metal oxide phase.

31. The method as claimed in claim 23, wherein the method of the invention is carried out in the absence of oxygen.

32. The method as claimed in claim 23, wherein the method includes removing oxygen from the mixture milling environment prior to milling.

33. The method as claimed in claim 23, wherein the absence of oxygen is achieved by substitution oxygen with a noble gas.

34. The method as claimed in claim 23, wherein the milled powder is used as feedstock for high velocity low temperature spray coating directly.

35. The method as claimed in claim 23, wherein the milled powder is compressed into a near-net shape of an orthopaedic part and sintered using conventional powder metallurgy method.

36. The method as claimed in claim 23, wherein the milled powder is formed to an orthopaedic component using fast prototyping techniques.

37. The method as claimed in claim 23, wherein heating of the mixture takes place at a temperature to enable the solid state reaction to take place.

38. The method as claimed in claim 23, wherein heating of the mixture takes place at a temperature exceeding substantially 5000° C.

39. The method as claimed in claim 23, wherein heating of the mixture takes place at or a temperature exceeding substantially 10000° C.

40. The method as claimed in claim 23, wherein the heating step takes substantially one hour.

41. The method as claimed in claim 23, wherein the heating step takes less than substantially one hour.

42. The method as claimed in claim 23, wherein the heating step takes longer than substantially one hour.

43. The method as claimed in claim 23, wherein the method includes the step of sintering the milled composite.

44. The method as claimed in claim 23, wherein the milling step can be varied in order to produce a composite of particular characteristics.

45. The method as claimed in claim 44, wherein it is the duration of the milling step that is altered.

46. The method as claimed in claim 44, wherein the step of milling the mixture is selected to produce a composite wherein the bioceramic phase and/or bioglass phase is present in substantially spherical particles distributed substantially uniformly throughout the metal phase.

47. The method as claimed in claim 44, wherein the step of milling the mixture is selected to produce a composite wherein the bioceramic phase and/or bioglass phase is present as substantially aligned elongate particles, dispersed substantially uniformly throughout the metal phase so as to comprise a laminate structure.

48. The method as claimed in claim 23, wherein in order to substantially assist osteointegration of the composite, the composite is substantially porous.

49. The method as claimed in claim 23, wherein in order to substantially assist osteointegration of the composite, the composite is substantially dense and becomes porous substantially porous in situ over time.

* * * * *